United States Patent [19]

Kawasaki

[11] 4,304,551
[45] Dec. 8, 1981

[54] TRACING DEVICE AND METHOD FOR RECORDING MANDIBULAR MOVEMENT

[76] Inventor: Tsugumichi Kawasaki, 432-8, Oaza Murasaki, Chikushino-shi, Fukuoka, Japan

[21] Appl. No.: 110,310

[22] Filed: Jan. 8, 1980

[30] Foreign Application Priority Data

Feb. 7, 1979 [JP] Japan .............................. 54-13154

[51] Int. Cl.³ ............................................. A61C 19/04
[52] U.S. Cl. ..................................................... 433/69
[58] Field of Search ................................. 433/69, 68

[56] References Cited

U.S. PATENT DOCUMENTS

| | | | |
|---|---|---|---|
| 2,334,898 | 11/1943 | Bigger et al. | 433/69 |
| 2,876,541 | 3/1959 | Jensen | 433/69 |
| 2,994,957 | 8/1961 | McLeod | 433/69 |
| 3,059,335 | 10/1962 | Reynolds | 433/69 |
| 3,068,570 | 12/1962 | Thompson et al. | 433/69 |
| 3,482,312 | 12/1969 | Smith | 433/69 |
| 3,562,106 | 7/1971 | Leathers | 433/69 |
| 3,778,902 | 12/1973 | Guichet | 433/68 |
| 4,055,896 | 11/1966 | Corbett | 433/69 |

*Primary Examiner*—Gene Mancene
*Assistant Examiner*—John J. Wilson
*Attorney, Agent, or Firm*—Jordan and Hamburg

[57] ABSTRACT

A tracing device for mandibular movement comprises mainly an upper jaw plate, a lower jaw plate and a coupling device, and the device is able to be mounted in the oral cavity of a patient regardless of whatever the patient is dentulous or edentulous. A recording method therewith can be carried out without elevation of the occlusal vertical dimension of a patient. An accurate recordiing of the jaw relation is taken by recording on the device an occlusal vertical dimension and an incisal guide angle which are settled in a prosthesis, and recording the mandibular position three dimensionally. Another feature of the device is to enable the reproduction of the record on the articulator. By recording the mandibular position and the mandibular movement with the device, the occlusal reconstruction based on the full mouth rehabilitation which has been regarded conventionally a most difficult prothesis method is carried out accurately.

3 Claims, 27 Drawing Figures

TRACING DEVICE AND METHOD FOR RECORDING MANDIBULAR MOVEMENT

BACKGROUND OF THE INVENTION

1. Field of the Invention

This invention relates to a tracing device for mandibular movement and a tracing method therefor.

More particularly, this invention relates to a tracing device for mandibular movement and a tracing method therefor, which can be carried out easily in a dental clinic to provide a centric jaw relation record and an eccentric movement record, even in the case of a patient whose oral cavity is either in a dentulous state or in an edentulous state.

This invention relates to a tracing device for mandibular movement and a tracing method therefor, which makes possible a centric jaw relation record and an eccentric movement record without requiring the elevation of the occlusal vertical dimension, especially even when the patient retains some healthy teeth.

2. Description of the Prior Art

Conventionally, it is already known that the record of jaw relation and mandibular movement in dental clinics have been carried out mainly by one of the following methods:

a. checkbite method,
b. panthograph method, and
c. chewing method.

Moreover, it is publicly known that many devices and methods to carry out the above mentioned methods concretely.

Among them, the checkbite method which utilizes the apex if a traced figure of a mandibular movement (so called Gothic arch) as a centric relation of a mandible and a point on a border moving path as a jaw position at an eccentric mandibular movement, and then fixes and records said jaw relations by means of the Christensen phenomenon is most widely used. It is publicly known that there are many kinds of devices to carry out the method as classified as follows:

(1) intraoral mandibular movement tracing devices, for example, Hesse, Sharry, Gysi, Messerman, Swenson, Gerber, Mc. Grane, Sosin, Okino and Oba, Nihon Dental University type, Bernea, Andresen, Bimeter, Granger and the like;

(2) extraoral mandibular movement tracing devices, for example, Gysi, Occlusolator, Okino and the like;

(3) intraoral and extraoral mandibular movement tracing devices which can be used cooperatively are, for example, Bimeter, Stansvery, Robinson, Hanau, Lott, Sears Trivet and the like.

However, originally most of the above mentioned devices have been developed to trace the mandibular movement of edentulous patients. Therefore, they have had many difficulties in practical use in clinics, when those devices were used on dentulous patients since every device could not be used without some elevation of the occlusion. They also had common defects in that the centric relation and/or the border moving path were recorded inaccurately.

Moreover, in addition to the above defects, the intraoral tracing devices had the following defects.

(1) It was difficult to observe the tracing at the centric jaw relation and the eccentric movement, and when the checkbite was taken, it was difficult to confirm whether a jaw relation was properly secured to a predetermined centric relation or an eccentric relation.

(2) The traced figure of the mandibular movement was relatively small and it was difficult to distinguish clearly the apex of the Gothic arch.

(3) Because the tracing pin served as a supporting nail (called support stud hereinafter) and as a tracing pin simultaneously, traced lines were relatively large and inaccurate. And also dependent on the position of the tracing pin which displaced the record base on which a tracing device was connected.

(4) As a result of the existence of the tracing device, patients often felt a sense of discomfort as their tongue was pressed by the tracing device interrupting the smooth movement of the mandible.

(5) In determining the settling position of the jaw relation, the devices necessitated repeated attachments and detachments in the course of operation, and there was a danger that resultant records could include errors.

SUMMARY OF THE INVENTION

The object of the invention is to provide a tracing device for mandibular movement and a method to take the record therewith mechanically and accurately by means of the checkbite method and which overcomes the above mentioned defects.

In accordance with the present invention, a tracing device for mandibular movement comprises:

an upper jaw plate, a lower jaw plate and a coupling device;

said upper jaw plate including a U-shaped upper jaw plate body, a support stud including a rotary ball and two auxiliary studs on said upper jaw plate body, and a pin fitting device which is provided projectively at the front end of said plate body;

said lower jaw plate including a lower jaw plate body, a tracing table and a guide table on said lower jaw plate body which form a tracing plate and a guide plate having slopes individually harmonized with the mandibular movement, said tracing table being provided with a forward inclination at the front end of the lower jaw plate body and said guide table being provided near the central portion of said lower jaw plate body and rearwardly of said tracing table;

said coupling device including a coupling shaft, an upper jaw plate support, a lower jaw plate support, and a two plates fixing screw, said coupling device being operable to vary the vertical distance between said two plates by means of said two plates fixing screw and to retain the coupled condition of the upper jaw plate and the lower jaw plate in a predetermined position by means of said coupling shaft.

Furthermore, in accordance with the present invention, the pin fitting device comprises a pin holding part, pins which are fitted into said holding part and including a cylindrical tracing pin, a jaw relation fixing pin, a tracing plate forming pin and the like, a helical spring for the pins, and a pin holding device consisting of a stopper for the pins, an elastic member and an elastic member stopper, and said pins being removably fitted to said cylindrical holding part.

Furthermore, in accordance with the invention, a method of recording the mandibular movement using a tracing device consisting of an upper jaw plate, a lower jaw plate and a coupling device which has a coupling and disassembly function for said jaw plates comprises the steps of:

according to the conventional manner, making an upper jaw record base and a lower jaw record base of a patient on a working casts of an upper jaw and a lower jaw which are mounted to an adjustable articulator;

coupling said lower jaw plate with the lower jaw plate support and then coupling said upper jaw plate with an upper jaw plate support by means of a coupling shaft, and as a result coupling the upper jaw plate with the lower jaw plate by means of said coupling device;

temporarily bonding the tracing device to the palatal portion of the upper jaw record base by means of a temporary bonding agent and after determining the position, coupling the upper jaw plate and the upper jaw record base by means of a bonding agent;

after closing the adjustable articulator, coupling the lower jaw plate with the lower jaw record base by means of the bonding agent;

releasing the coupling shaft and after opening the adjustable articulator, removing the coupling device from the lower jaw plate and finishing the coupling of the two plates on the record bases individually for the preparation for a recording;

according to the conventional manner, fixing the record bases of the upper jaw and the lower jaw to which the tracing device is assembled to teeth or to alveolar ridges in the oral cavity by means of an adhesive;

adjusting the positions of a guide support stud and a guide plate by shifting the lower jaw plate body;

after completing the adjustment of the occlusal vertical dimension, putting a plastic material on a guide plate and having the patient carry out the mandibular movement, forming a mandibular movement path and recording thereof;

furthermore, putting the plastic material on moving path forming tables, forming movement paths records by means of movement path forming auxiliary studs and recording thereof;

after inserting a tracing plate forming pin into a pin holding part, putting the plastic material on a tracing table, and forming a tracing plate having a slope by means of the tracing plate forming pin;

tracing a mandibular moving path on the surface of the tracing plate by means of a tracing pin and making small holes on the line of the mandibular moving path to fix the jaw relation;

fixing the jaw relation by fitting a jaw relation fitting pin into the small holes;

providing a contact having electric conductivity to the plate facing said jaw relation fixing pin, and then confirming a fixed condition of the jaw relation by means of an electric resistor;

and according to the conventional manner, pouring a material for checkbite between the upper jaw record base and the lower jaw record base, taking a checkbite core, adjusting the adjustable articulator using the obtained check-bite core, and as a result, replacing the records taken at the centric jaw relation and the border mandibular movement which is recorded in the oral cavity of the patient on the adjustable articulator.

BRIEF DESCRIPTION OF THE DRAWINGS

The invention is described in detail hereinafter in connection with the drawings in which:

FIG. 1b is a diagramatic sectional view taken along line 1A—1A of FIG. 1a;

FIG. 2b is a diagramatic sectional view taken along line IIA—IIA of FIG. 2a;

FIG. 3b is a diagramatic sectional view taken along line IIIA—IIIA of FIG. 3a;

FIG. 3e is a side section taken along line IIIA'—IIIA' of FIG. 3a;

When this invention is practiced, it has the following advantages.

(1) When the tracing device is used, since an elevation of the occlusal vertical dimension is not necessary, a record of high precision can be obtained.

(2) In cases in which healthy teeth remain in a dentulous jaw, because the tracing is possible only by insuring the vertical intermaxillary distance, a record of high precision can be obtained.

(3) In the tracing operation, the Gothic archs at the centric jaw relation and the eccentric movement are visible directly. And also a checkbite core will be taken, it is easily confirmed whether a jaw relation is fixed accurately into a settled position or not by means of the operator's naked eye or the electric resistor 200. There are no mistakes in tracing and a record of high precision can be obtained.

(4) The Gothic arch is traced precisely by means of the tracing pin 1, and the apex is distinguished clearly. Consequently, the jaw relation and eccentric movement are settled easily and precisely.

(5) The patient is able to move his mandible to a centric relation by natural muscular power. Accordingly, the operator can obtain a record of high precision, and moreover it is not necessary to learn special skills.

(6) Because the change of an occlusal vertical dimension and the adjustment of the guide plate 10a can be made easily on the tracing device in an oral cavity, a record of high precision can be obtained and the record is usable for an occlusal equilibration such as removal of occlusal interference and the like.

(7) Because the tracing device provides a plurality of studs which retain an occlusal vertical dimension, the two record bases X, Y show good stability. Furthermore, because a checkbite core is taken with an occlusal pressure less than that in the prior art, a record of high precision can be obtained.

(8) Once the tracing device is mounted in the oral cavity of a patient, removal and mounting of said device are not necessary. Consequently, the operator can obtain a record without errors which may be a result of repeated removals and mountings, and therefore a record of high precision can be obtained.

(9) The operator can carry out the operation easily which the tracing device to the record bases X, Y is situated on the adjustable articulator 100. Also, he can carry out easily and precisely the operation of the tracing device in the case of the adjustable articulator 100 is adjusted after a checkbite core is taken.

(10) The tracing device is usable in every case in which the condition of the oral cavity is edentulous or dentulous. Consequently, the device can be applied to every case which necessitates prosthetic treatment and occlusal equilibration, and the device has wide utilization.

(11) Because the tracing device is small in size and light weight, said device causes less pressure on the tongue, and the patient feels less discomfort. Thus, smooth mandibular movement produces a record of high precision.

DESCRIPTION OF THE PREFERRED EMBODIMENT

In the accompanying drawings FIGS. 1 to 5, the tracing device according to this invention is shown by elevational or plan views and by assembled or exploded conditions.

Figure 6:
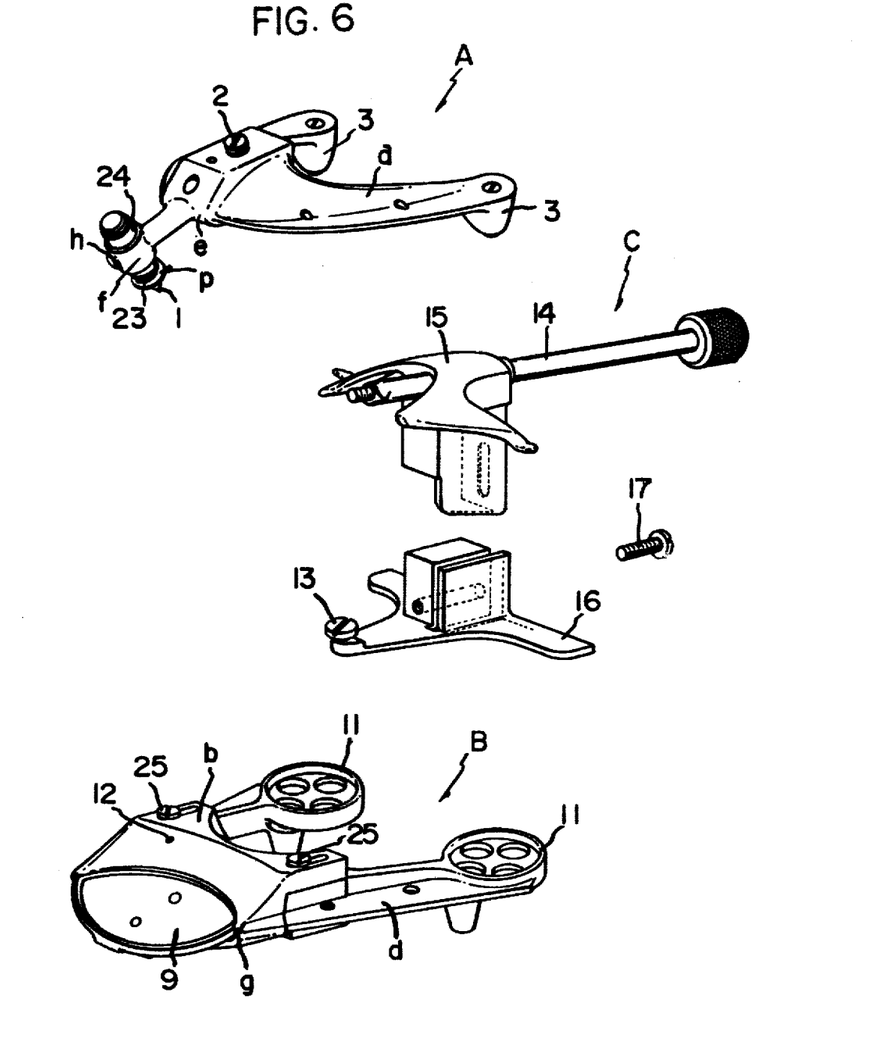
FIG. 6 is a perspective view of the tracing device according to the present invention shown in FIG. 1a to FIG. 1c, which is exploded to each members.

In FIG. 6, the tracing device is shown by a perspective view in which each member is arranged in order.

Figure 7:
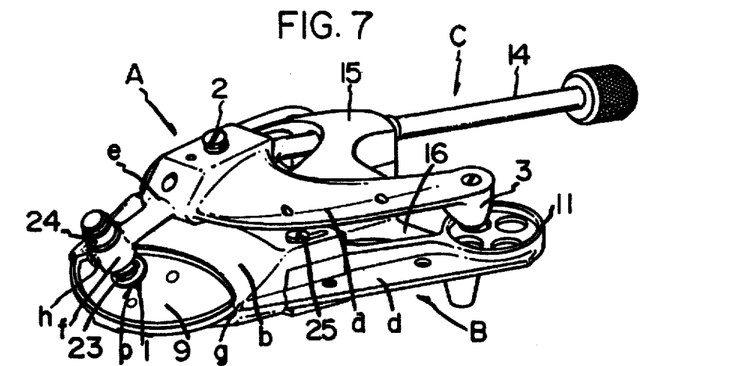
FIG. 7 is a perspective view of said device after being assembled.

In FIG. 7, the tracing device is shown by a perspective view in which said members are assembled.

Figure 8:
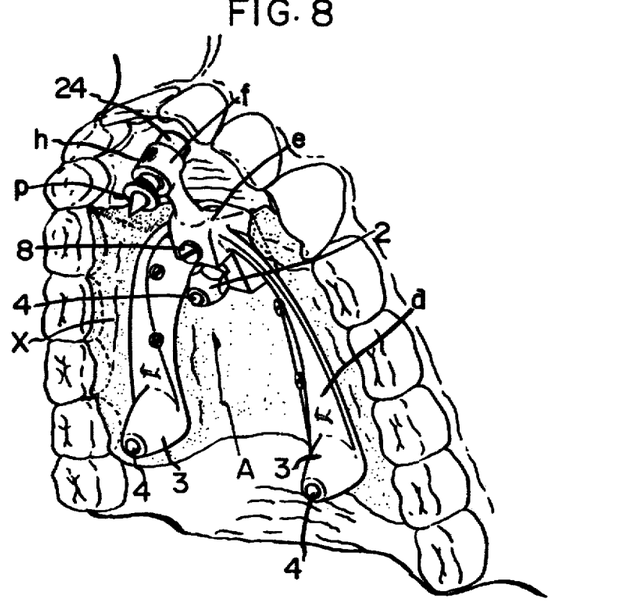
FIG. 8 is a perspective view of the upper jaw plate which is fitted into an upper jaw.

In FIG. 8 an upper jaw plate is shown by a perspective view which shows a fitting position thereof in an upper jaw.

Figure 9:
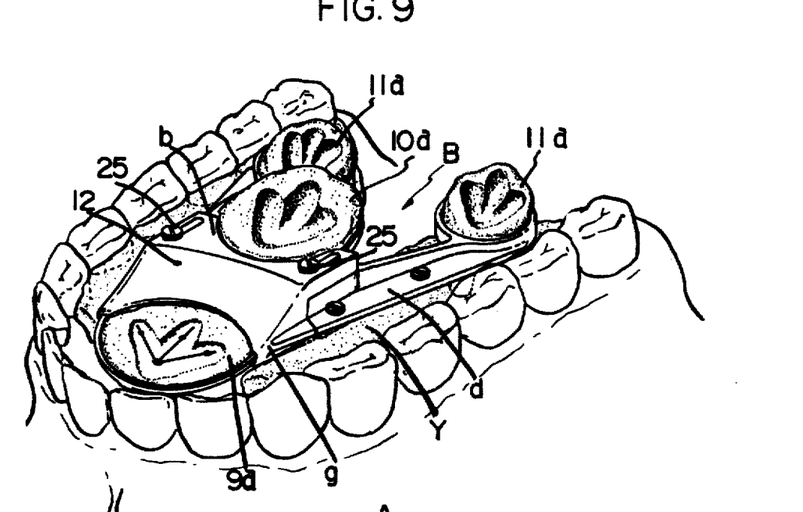
FIG. 9 is a perspective view of the lower jaw plate which is fitted into a lower jaw.

In FIG. 9, a lower jaw plate is shown by a perspective view which shows a fitting position thereof in a lower jaw.

Figure 10:
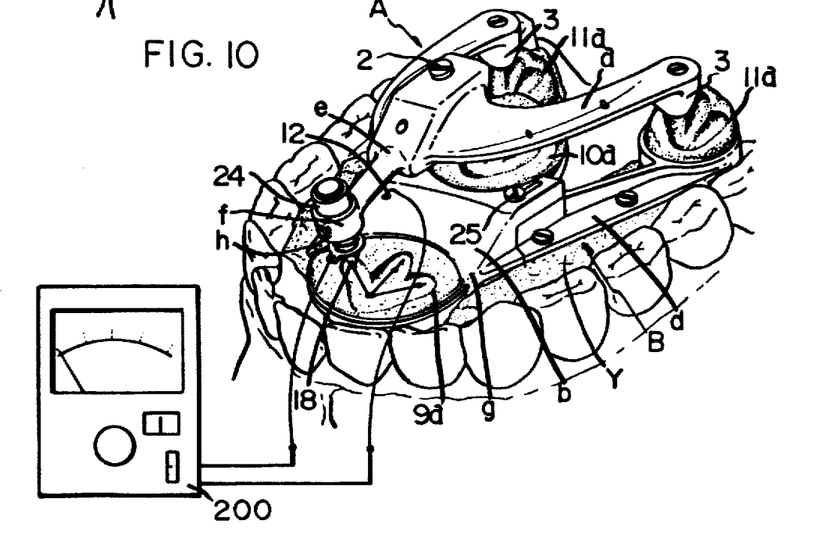
FIG. 10 is a diagramatical view showing the state of the tracing device according to the invention in an oral cavity in which metal wires are connected to a pin and to a metal wire connecting part individually, and then each wire is connected to an electric resistor.

In FIG. 10, there is shown the diagramatical view in which two metal wires are connected to a pin and to a metal wire connecting part according to the invention and also connected to an electric resistor.

Figure 11:
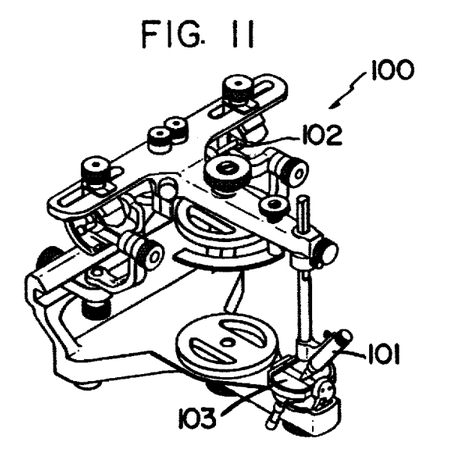
FIG. 11 is a perspective view of examplified adjustable articulator which is used in combination with the tracing device according to the invention.

In FIG. 11, an example of an adjustable articulator which is used in combination with the tracing device according to the invention is shown.

Generally, adjustable articulators are machines which reproduce the position of the condyle head and glenoid cavity and the direction and angle which the condyle head moves along the glenoid cavity. And the machines are primarily used in the case when prosthesis such as artificial dentures are formed and marketted about scores kinds of them.

The adjustable articulator shown in the drawing is "UNIVERSITY ARTICULATOR Model 130-21, Hanau Co., Ltd.".

In the drawing, the numeral 101 designates an incisal pin. The numeral 102 designates a condylar element. The numeral 103 designates an incisal guide table.

Figure 2A:
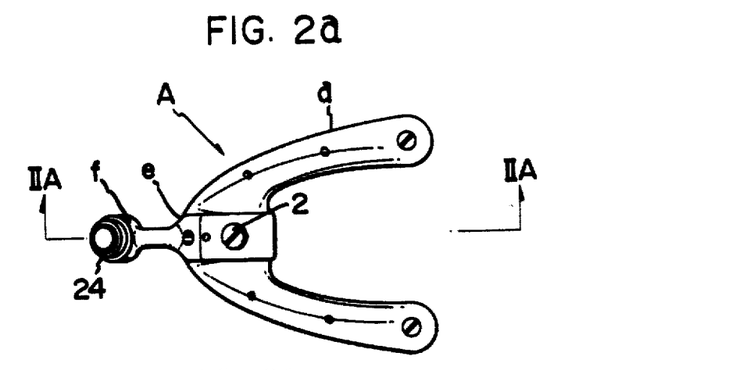
FIG. 2a is a plan view of the upper jaw plate.
Figure 2B:
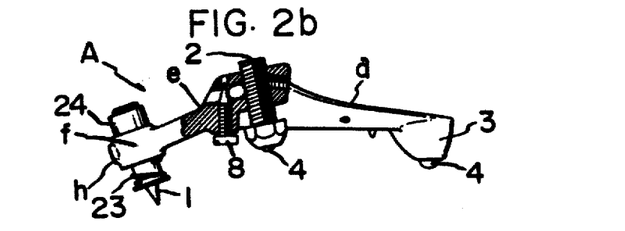

In the drawings FIGS. 2a to 2b, the upper jaw plate A consists of a tracing pin 1 which is provided to trace mandibular movement and is detachably fitted, a guide support stud 2 which is provided to guide the mandibular movement and to retain an occlusal vertical dimension and is adjustable along its length freely, and two moving path forming auxiliary studs 3, which are provided to form a mandibular moving path and are fixed.

Figure 1A:
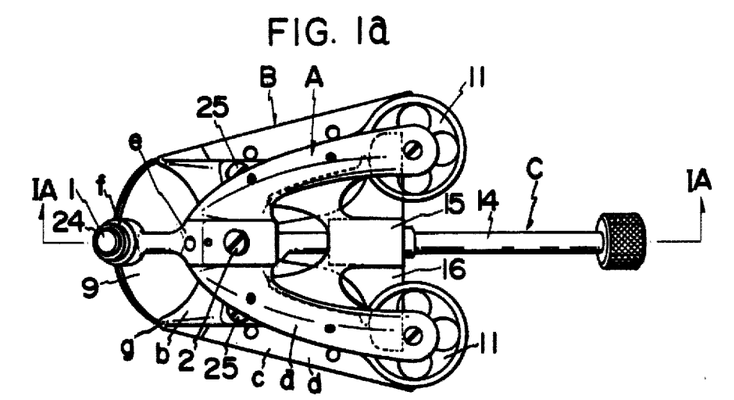
FIG. 1a is a plan view of the tracing device according to the present invention which shows an upper jaw plate and a lower jaw plate connected by a coupling means.
Figure 1B:
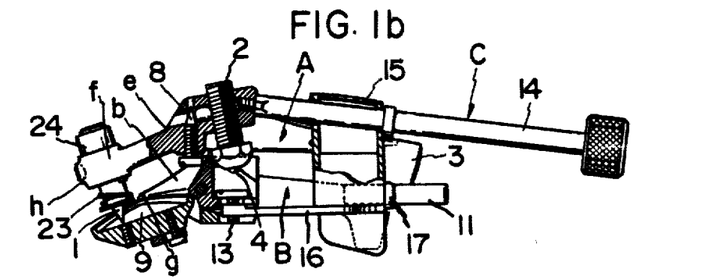
Figure 1C:
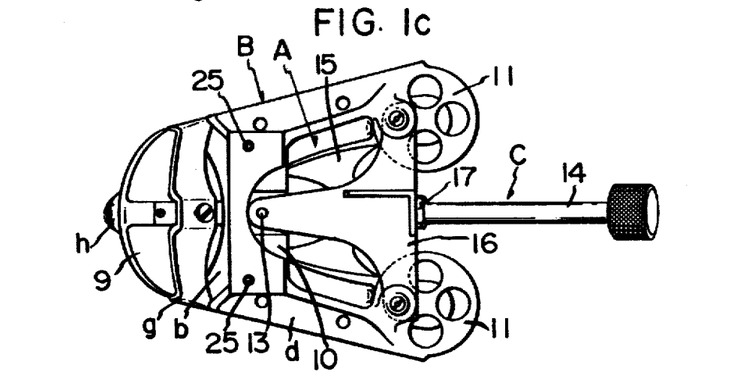
FIG. 1c is a rear view of the tracing device.

As seen in FIGS. 1b and 2b, in each guide support stud 2,3,3 rotary balls 4 are fitted therein.

Figure 2C:
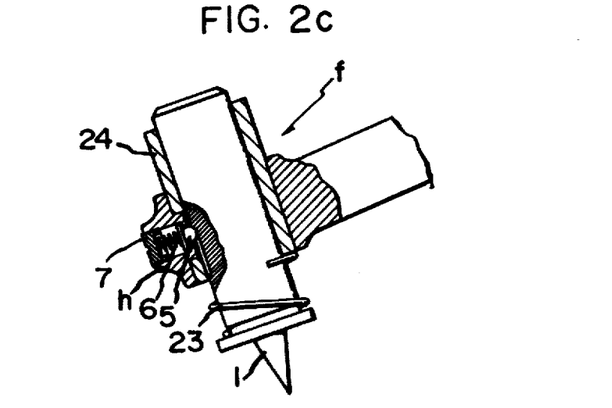
FIG. 2c is a partially enlarged section of the pin fitting device.

Furthermore, as seen in FIG. 2c, in the front of an upper jaw plate body a, there is provided a stopper for pins 5, an elastic member 6, and an elastic member stopper 7, constituting a pin holding device h which seves to detachably retain the tracing pin 1 and to hold the tracing pin 1 therein correctly.

As seen in FIG. 2b, in the middle of the plate body a, there is provided a stud fixing screw 8 which serves to fix the guide support stud 2.

Figure 3A:
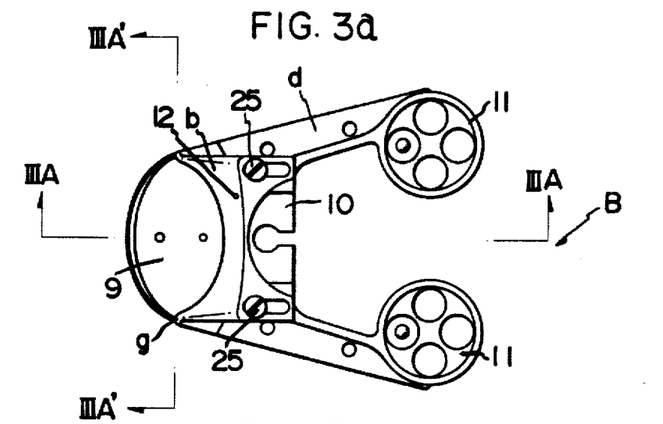
FIG. 3a is a plan view of the lower jaw plate.
Figure 3B:
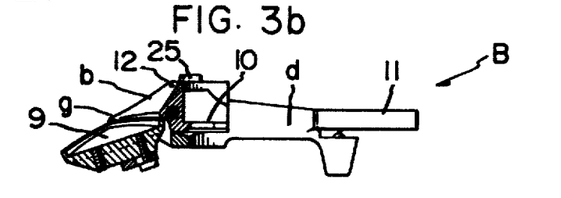
Figure 3C:
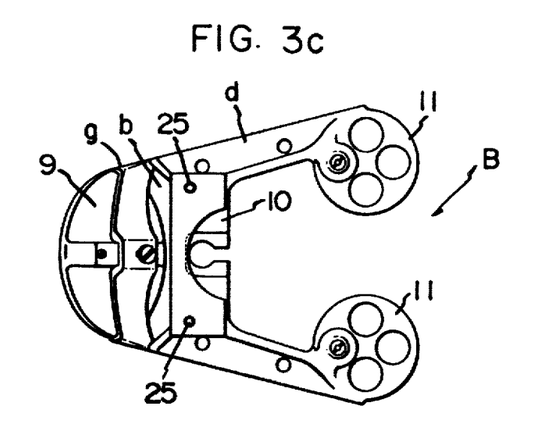
FIG. 3c is a bottom plan view of the lower jaw plate.
Figure 3D:
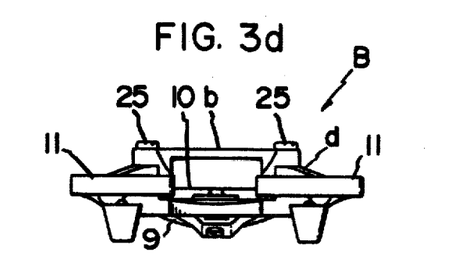
FIG. 3d is a rear view of the lower jaw plate.
Figure 3E:
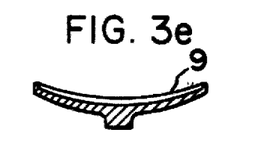
Figure 3F:
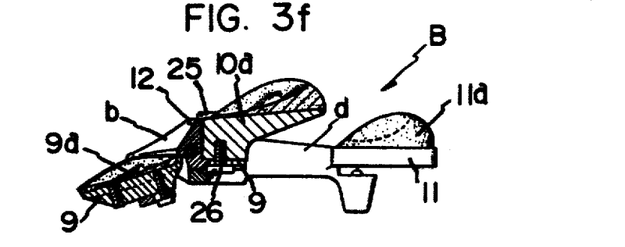
FIG. 3f is a side section of the lower jaw plate on which a tracing plate, a guide plate and a mandibular movement path are formed.

As shown in FIGS. 3a to 3b, four tables 9, 10, 11, 11 are provided on the lower jaw plate B. The table 9 is a tracing table which acts as a table to form a trading plate 9a on which a Gothic arch will be traced facing to the tracing pin 1. A guide table 10 which records an incisal guide angle which is provided inherently on the patient and acts as a table to form a guide plate 10a facing the guide support stud 2. The tracing table 9 and guide table 10 constitutes a lower jaw plate body b, and said lower jaw plate body is coupled with a record base coupling part d of the lower jaw plate B by means of lower jaw plate body fixing screws 25, 25.

Also, two moving path forming tables 11, 11 which act as tables to form the patient's mandibular moving paths 11a, 11a three dimensionally face two moving path forming auxiliary studs 3, 3 individually. Furthermore, on both front sides of the guide table 10, there are provided metal wire connecting part 12 to fix metal wires which are connected to an electric resistor 200.

Figure 4A:
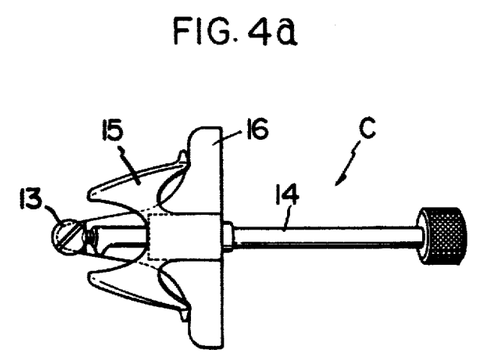
FIG. 4a is a plan view of the coupling device.
Figure 4B:
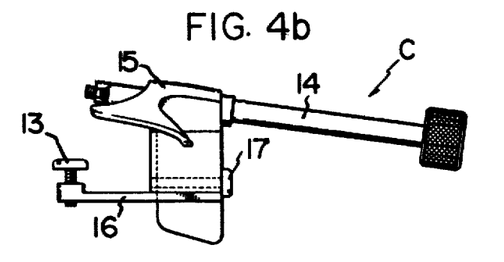
FIG. 4b is a diagramatic left side view of the coupling device which is shown partially exploded.
Figure 5A:
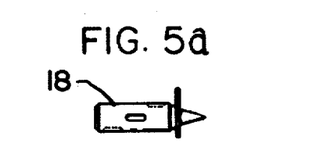
FIG. 5a is an elevational view of a jaw relation fixing pin.
Figure 5B:
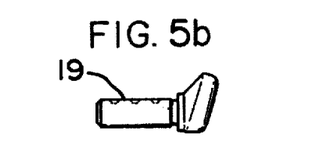
FIG. 5b is an elevational view of a tracing plate forming pin.
Figure 5C:
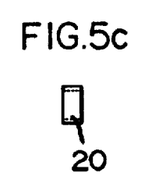
FIG. 5c to FIG. 5e are elevational view of spacers for the pins.
Figure 5D:
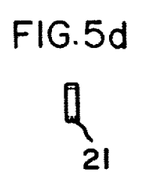
Figure 5E:
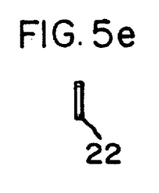
Figure 5F:
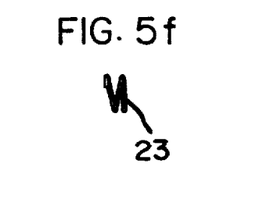
FIG. 5f is an elevational view of a helical spring for the pins.

As shown in FIGS. 4a and 4b, the coupling device C is constituted from a plate coupling shaft 14, an upper jaw plate support 15 and a lower jaw plate support 16. The upper jaw plate support 15 and the lower jaw plate support 16 are coupled to each other by a two plate fixing screw 17. Also, the coupling between the upper jaw plate A and the upper jaw plate support 15 is carried out by the coupling shaft 14. The coupling between the lower jaw plate B and the lower jaw plate support 16 is carried out by a coupling screw 13.

As shown in FIGS. 5a to 5f, parts of the tracing device according to the invention are constituted from a jaw relation fixing pin 18 which serves to fix the jaw relation to a predetermined position, a tracing plate forming pin 19 which serves to form the tracing plate 9a, spacers for pins 20, 21, 22 which serve to change the lengths of the pins, and a helical spring 23.

The tracing device and the tracing method according to the invention will be further described with reference to the example.

EXAMPLE

According to the conventional manner, after an operator makes an upper jaw record base X and a lower jaw record base Y which are designed in response to the case of a patient so that they do not disturb the maintenance of the occlusal vertical dimension of each other, working casts of an upper jaw and a lower jaw are mounted to an adjustable articulator 100 at a temporary centric jaw relation. Then a tracing device is assembled on an upper jaw plate A and a lower jaw plate B by means of a coupling device C. The assembled tracing device is coupled and fixed to the upper jaw record base X. However, preceding said procedure the distance between the upper jaw plate A and the lower jaw plate B is adjusted in response to the case of the patient.

For example, in a case where the tracing device is used for an occlusal equilibration or a case where a temporary centric relation are set highly, because the operator adjusts an occlusal vertical dimension by lowering it in the oral cavity, he is required to insure some previous space. Also in such case he is not required to change the vertical occlusal dimension or in such case he must elevate somewhat the vertical occlusal dimension in the oral cavity and the like, and he adjusts the space between the upper jaw plate A and the lower jaw plate B to a minimum distance.

To the end of these adjustments, the tracing device according to the invention has the feature that the operator can easily adjust the vertical occlusal dimension with an assembled condition of said device by means of the two plates fixing screws 17 as shown in FIGS. 1b, 4b and 6, and by confirming the moving distance in a space with his naked eye.

Next, the tracing device is temporary mounted on the upper jaw record base X by means of a temporary mounting agent such as rubber, putty and the like. At that time, the mounting position of the upper jaw plate A is determined by taking care so that said plate A is positioned parallel to an occlusal plane, a front and central part and palatal side. In the above mounted condition, the operator confirms the adjustable articulator 100 by opening and closing said articulator whether the tracing device is located to a suitable position in relation to a mandibular working cast.

Assuming that in an opening and closing action of the adjustable articulator 100, when a portion of the tracing device contacts a working cast for the mandible or space for the tongue room is not sufficient, the operator determines an optimum position by integrally shifting the assembled tracing device front and back, right and left, up and down.

When the position is determined the upper jaw record base X and the upper jaw plate A are fixed by a bonding agent such as instantaneous polymerizable resin.

Next, the tracing device is temporarily mounted by placing a block of adhesive such as putty on the lower jaw record base Y and then closing the adjustable articulator 100 until the working casts for the upper and the lower jaw insure a predetermined occlusal vertical dimention.

Thus, the tracing device can be located at an optimum position in the space of working casts for the upper and lower jaw which also corresponds to the optimum position in the oral cavity. Next, it is necessary to detach the coupling of the upper jaw plate A and the lower jaw plate B without changing this settled position, especially without influencing the lower jaw plate which is temporarily mounted. Therefore, the tracing device according to the invention can complete the above object only by releasing the coupling by rotating the knob of the coupling shaft 14.

That is, when the adjustable articulator 100 is opened after the coupling is released, the upper jaw plate A is fixed to the upper jaw record base X, and the lower jaw plate B is temporarily mounted on the lower jaw record base Y. After the lower jaw plate B and the lower jaw record base Y are fixed tightly to each other by a bonding agent such as instantaneous polymerizable resin, the lower jaw plate B and the coupling device C are separated individually by releasing the plate coupling screw 13 and pushing back the coupling device C.

In the conventional tracing devices for intraoral, extraoral, and intraoral-extraoral combined uses, there was not seen any coupling instrument which could be carried in a coupled condition of an upper jaw plate and a lower jaw plate. Therefore, for example, there had been carried out a coupling method to the record bases by the following procedure from (1) to (4):

(1) a tracing plate is coupled to an upper jaw record base or a lower jaw record base;

(2) a suitable spacer is placed thereon;

(3) a plate having a tracing pin is mounted on said spacer and insures a height between plates;

(4) thereafter, the plate having the tracing pin is coupled to the record base.

As a result, the tracing device was inferior in operational characteristics, difficult to locate at an optimum space in an oral cavity, and pressed against the tongue.

The tracing device according to the invention has features that removed the above mentioned defects by using a special releasing means in the coupling device C. Said means elevate the operational characteristics and accuracy when said device is coupled to a record base.

Figure 3G:
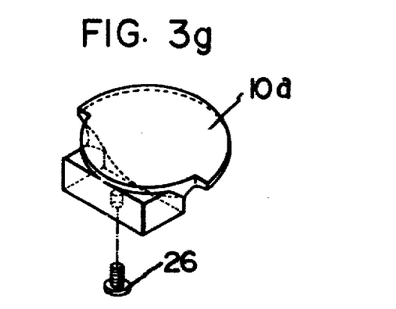
FIG. 3g is a perspective view of the guide plate.

And then the guide plate 10a shown in FIG. 3g is coupled to the guide table 10 by means of a guide plate fixing screw 26.

Next, as shown in FIGS. 8 and 9, the tracing device and the record bases X, Y are fixed to the teeth or alveolar ridges by means of adhesive such as cement.

Subsequently, the jaws of the patient are occluded, and when a gap is caused between the guide support stud 2 and the guide plate 10a, the operator carries out the adjustment by releasing the lower jaw plate body fixing screw 25 and then moving the lower jaw plate body b back and forth.

Subsequently, an occlusal vertical dimension is ascertained. When the operator is required to change the vertical dimension, he carries out a microadjustment of the vertical dimension by means of a screw of the guide support stud 2, and if the height is determined he fixes it by screwing the stud fixing screw 8.

The operator then guides the mandible of the patient forward and laterally and traces a Gothic arch on the guide plate 10a by means of the guide support stud 2, and he forms an incisal guide angle which is inherent to the patient by the operation such as addition and grinding and records on the guide plate 10a.

The conventional tracing devices of intraoral, extraoral, and intraoral-extraoral combined types did not provide any mechanism which records an inherent incisal guide angle of each patient and a pin for tracing was slid only on a plane plate. Therefore, in a dentulous case, it was difficult to trace a Gothic arch without insurance of the vertical dimension between one set of opposed teeth by an elevation of the occlusal vertical dimension and an obstruction to contact of the teeth. Therefore, the cases which could be traced were limited and the prior art was not practical for use in clinics.

In the tracing device according to the invention, the upper jaw plate A has a U-shaped form which is notched from the central portion to the rear portion thereof. Accordingly, without requiring an elevation of the vertical distance between the upper jaw plate A and the lower jaw plate B a space which can be the guide plate 10a is insured. Additionally, the weight of the upper jaw plate A can be reduced.

Also, in the tracing device according to the invention, the guide table 10 and the tracing table 9 do not exist on a same plane so that makes it possible for the operator to directly observe the situation of the guide plate 10a and the Gothic arch traced on the tracing plate 9a and to carry out correctly the work which guides the mandibular movement and the like, and said tracing table is located in front and downwardly. Thus, the tracing device has merits in that the whole said device is mounted palatinalis and the various obstructions which are caused by pressure on the tongue are reduced.

Furthermore, in the case the operator lets carrying out of the mandibular movement to the patient when there will occur a bad influence on the patient's nervous and muscular mechanism, it is difficult to obtain an accurate record. Therefore, rotary balls 4 are included in the guide support stud 2 and the moving path forming auxiliary studs 3, 3 individually, and the tracing device is constructed so that it is possible to obtain a smooth sliding movement thereof and to reduce the resistance of the mandibular movement.

Also, the tracing device has the feature that because an inherent sense of teeth is completely interrupted by the work forming the guide plate 10a, such difficulties that the Gothic arch being confused or the tracing of the Gothic arch being impossible are resolved.

And then, a plastic material such as putty-like silicone rubber is placed on the moving path forming tables 11, 11. And mandibular moving path records 11a, 11a which harmonize with the patient's mandibular movement are formed by means of the guide support stud 2 and the guide plate 10a.

Heretofore, the conventionsl devices for intraoral, extraoral, and intraoral-extraoral combined constructions in which pins for tracing or support studs were contacted with the plane tracing plates vertically. Therefore, it was not normal to give excess sliding movement by the provision of the rotary balls 4 in the guide support stud 2 because central relations were made obscure by the confusion thereof or movement records were instable.

But the tracing device according to the invention makes possible a positive sliding movement by including the rotary balls 4 in the guide support stud 2 based on the following clinical results:

(1) the mandible is not pushed from a central relation backwards with a relaxed natural muscular force of the patient himself, even if an excessive sliding movement is given to the guide support stud 2 by the rotary balls 4 and the like, and (2) because the guide plate 10a which is opposed to the guide support stud 2 forms a slope which harmonized with the incisal guide angle and the condyle path inclination, the forward and lateral push of the mandible is inhibited and liable to concentrate to a point.

As a result, a movement to push the mandible forward is obstructed and while a force which guides the mandible rearward acts, therefore an effect is caused which stabilizes the mandible to a centric relation by the relaxed natural muscular force of the patient without depending on the operator's guide. Thus, the tracing device according to the invention has the feature which makes it possible to record an accurate centric relation.

On the other hand, because the plurality of studs contact to the mandibular moving path records 11a and guide plate 10a, the record bases X, Y are stabilized and also directions at the border movement of the mandible are stabilized, the tracing device according to the invention has the feature that the Gothic arch contains no disturbance and an accurate tracing is obtained.

Next, after a tracing plate forming pin 19 is inserted into a pin holding part 24, a plastic material such as instantaneous polymerizable resin is placed on the tracing table 9. And guiding the mandible of the patient, a sector like inclination which harmonizes to the patient's incisal guide and condyle path is formed by means of the tracing plate forming pin 19, and thus the tracing plate 9a is formed.

Furthermore, said guide plate and said tracing plate can be formed by operating the adjustable articulator 100, or a ready made inclination plate may be utilized.

Next, the tracing pin 1 is inserted into the cylindrical holding part 24. Assumably when there will be some distance between the tracing pin 1 and the tracing plate 9a by an elevation of the occlusal vertical dimension, the length of said pin can be changed by means of pin spacers 20, 21, 22 without changing the elasticity of said pin.

Subsequently, the operator inserts the tracing device into the oral cavity of the patient and moves the patient's mandible forward and laterally and traces a border movement path while regarding a tracing point as the starting point. In the course of the tracing, a constant pressure is added on the tracing plate 9a by means of the elasticity of the helical spring 23 which is provided within the tracing pin 1.

Furthermore, in order to record a Gothic arch accurately and to fix the settled jaw relation correctly, it is required that no play or shaking exists and that the pins are highly accurate. To accomplish this aim, an accurate tubular cylinder and the cylindrical pins p are combined together. Thus, the tracing device has the feature that the pins are miniaturized.

It is known publicly that the conventional intraoral tracing devices, extraoral tracing devices or intraoral-extraoral tracing devices have mechanisms which trace mandibular movements by means of tracing pins provided with elasticity. Because said mechanism have constructions in which the tracing pins provided with elasticity vertically contact for plane tracing plates have defects as follows.

(1) In a Gothic arch which will be traced by a tracing pin which is provided with elasticity, there is added an upward and downward movement of the tracing pin following the mandibular movement at the recording thereof. In short, the tip of the tracing pin is moved together with the mandible and furthermore projected in the direction of the tracing pin. Accordingly, the angle which is formed between the tracing pin and the tracing plate is continuously changed at a mandibular movement, the Gothic arch by means of the tracing pin which is provided with elasticity at a mandibular movement may be called a distorted virtual image of a practical moving path.

(2) When a conventional tracing device is occluded at a centric relation, a tracing pin which is most elongated by elasticity provided in said pin will touch the tracing plate before a mandible is guided to the centric relation completely. Therefore, a moving pathlike tracing figure is traced between a point which is touched at first by said pin and a correct centric relation, and said figure looks as if there is a gap between the centric relation and the centric occlusion.

(3) In the conventional tracing devices, as the tracing figure is often traced extraorally, a moving path is enlarged. Also, in such a case that the shaking of the record base will be caused at a tracing, in addition to the above mentioned error an error due to the tracing is supplemented.

The tracing device according to the invention has the following features in order to improve the defects of the conventional tracing devices.

(1) The tracing plate 9a provides a slope which harmonizes with the incisal guide angle which is inherent in a patient.

(2) A tracing pin is settled about vertically to the slope forming an arrow like surface.

(3) The pressure of the spring is designed to require the lowest limit and a limitation is given to an upward and downward moving range of the tracing pin by means of the pin holding device h.

Thus the tracing device protects from variations in the angle, length and pressure of the tracing pin 1 which touches to the tracing plate 9a depending upon the mandibular position at mandibular movement.

Also, the tracing device according to the invention has the features that the Gothic arch is traced comparatively large, an angle of the Gothic arch is formed to a more acute angle than that traced on a conventional plane surface, the condition of the tracing is easily observed, and a determination of the mandibular relation is carried out accurately and precisely, by the reasons as follows:

(1) because the tracing is made in an oral cavity, the real dimension of the mandibular movement is traced;

(2) in the oral cavity, the tracing pin 1 and the tracing plate 9a are positioned forwardly; and (3) the tracing plate 9a is formed as a slope which harmonizes with the mandibular movement.

Next, a mandibular relation at a centric relation and an eccentric movement relation is determined. In said positions a small hole in which the needle point of the jaw relation fixing pin 18 will be fitted is bored. In the case that there exists several natural teeth in a patient's oral cavity that are invisible from the exterior, a small hole of the tracing plate 9a is bored until said hole is penetrated to the metal surface of the tracing table 9.

Subsequently, instead of the tracing pin 1, the jaw relation fixing pin 18 is inserted into the pin holding part 24, and the jaw relation fixing pin 18 is fitted into the small hole by guiding the mandible. Keeping up the condition of said jaw relation, according to the conventional manner, a checkbite is taken with the use of materials such as plaster.

In the tracing device according to the invention, the jaw relation fixing pin 18 is separate in its function from that of the guide support stud 2 retaining the occlusal vertical relation. Therefore, the tracing device has the feature that the vertical relation is not changed at all when the mandible will be fixed by the jaw relation fixing pin 18.

In the case of a patient where several natural teeth exist in the front portion and a position of the small hole is invisible from the exterior, it is difficult to ascertain whether the jaw relation fixing pin 18 is fitted correctly in the small hole on the tracing plate 9a or not. There is adapted the method of ascertainment which utilizes an electric resistor 200 in the tracing device.

In short, a metal wire is connected to the jaw relation fixing pin 18, and another metal wire is connected to the metal wire connecting part 12. These two metal wires are extended extraorally using spaces between the teeth, and said wires are connected to the electric resistor 200 individually.

In the small hole on the tracing plate 9a, a material such as electroconductive fluid is filled. When a jaw relation fixing pin 18 is fitted in the small hole by guiding the patient's mandible, this place forms a contact which has only electroconductivity between the upper jaw plate A and the lower jaw plate B. A meter of the electric resistor 200 shows a resistance value instantaneously and the fitting of said pin 18 is indicated. For reasons stated above the tracing device according to the invention has features that make said device usable for dentulous patients. The mandibular relation at centric relation and eccentric movement are determined accurately, and a checkbite is taken by accurately fixing the determined mandibular relation.

Next, the adjustment of the adjustable articulator 100 is carried out making use of the checkbite core. At first, the guide support stud 2 is adjusted to a short length, after the mandibular moving path records 11a, 11a on the moving path forming table 11, 11 are removed, a working cast for the mandible is temporarily mounted thereon by using a checkbite core at the centric relation.

Similarly, according to the conventional manner, a condyle path inclination of the adjustable articulator 100 is adjusted by using a checkbite core at the eccentric movement.

Subsequently, the guide support stud 2 is returned to the same height as that of the recording in the oral cavity and the height is fixed by means of the stud fixing screw 8. An incisal pin 101 of the adjustable articulator 100 is removed, and the operator makes lateral movements with the adjustable articulator 100 by retaining an occlusal vertical dimension by means of the guide support stud 2. At that time, it is ascertained whether the tracing pin 1 travels on the line of the Gothic arch traced on the tracing plate 9a or not. If when said tracing pin travels in a position separated from the line, a condylar element 102 at the working side of the adjustable articulator is moved right and left, and a rotating central shaft at the working side is determined by changing the distance between the condyles.

Next, after the incisal pin 101 of the adjustable articulator 100 is returned to the original position, the angle of the incisal guide table 103 of the adjustable articulator 100 is adjusted to suit the angle of the slope of the guide plate 10a.

After completing all adjustments on the adjustable articulator 100, the working cast of the mandible is remounted to said articulator and all operations concerning the tracing device are completed.

In the conventional intraoral tracing device, it is impossible to trace again the Gothic arch traced in an oral cavity and an incisal guide angle recorded in the oral cavity on the course which the adjustable articulator 100 is adjusted and to trace again in the adjustable articulator 100. While the tracing device according to the invention enables those operations and therefore said device has the features that it increases a range of utilization of the adjustable articulator 100 and elevates the accuracy when the adjustable articulator 100 is adjusted by the checkbite method.

Furthermore, when the conventional intraoral, extraoral and intraoral-extraoral tracing device is used, an operator must repeat the detachments and attachments of said device in the patient's oral cavity; and the operator increases the risk factor which includes errors as the number of detachments and attachments increases. Accordingly, once the tracing device according to the invention is mounted into the oral cavity, said device provides the construction by which all work is carried out in the oral cavity. As a result, especially in dentulous cases, said device has the feature that accuracy is elevated significantly.

When the tracing device according to the invention is used in connection with a pantograph because the recording is able to obtain at least the required occlusal vertical dimension, said device has the feature that the accuracy of the record depending on the pantograph is elevated further and the range of application is widened.

What is claimed is:

1. A tracing device for mandibular movement comprising:

an upper jaw plate, a lower jaw plate and a coupling device;

said upper jaw plate including a U-shaped upper jaw plate body, a support stud having a rotary ball and two auxiliary studs on said upper jaw plate body, and a pin fitting device which is provided projectively at the front end of said plate body;

said lower jaw plate including a lower jaw plate body, a tracing table and a guide table on said lower jaw plate body which form a tracing plate and a guide plate having slopes individually harmonized with the mandibular movement, said tracing table being provided with a forward inclination at the front end of the lower jaw plate body and said guide table being disposed near the central portion of said lower jaw plate body and rearwardly of said tracing table;

said coupling device including a coupling shaft, an upper jaw plate support, a lower jaw plate support, and a fixing screw, said coupling device being operable to vary the vertical distance between said two plates by means of said fixing screw and to retain the coupled condition of said upper jaw plate and said lower jaw plate in a predetermined position by means of said coupling shaft.

2. The tracing device according to claim 1, wherein said pin fitting device comprises a pin holding part, pins which are fitted into said holding part and including a cylindrical tracing pin, a jaw relation fixing pin, and a tracing plate forming pin, a helical spring for the pins, and a pin holding device consisting of a stopper for the pins, an elastic member and an elastic member stopper, said pins being removably fitted to said cylindrical holding part.

3. A method of recording the mandibular movement using a tracing device consisting of an upper jaw plate, a lower jaw plate and a coupling device which has a coupling and disassembling function for said jaw plates comprising the steps of:

making an upper jaw record base and a lower jaw record base of a patient on working casts of an upper jaw and a lower jaw which are mounted to an adjustable articulator;

coupling said lower jaw plate with said lower jaw plate support and then coupling said upper jaw plate with an upper jaw plate support by means of a coupling shaft, and as a result coupling the upper jaw plate with the lower jaw plate by means of said coupling device;

temporarily bonding the tracing device to the palatal portion of the upper jaw record base by means of a temporary bonding agent and after determining the position, coupling the upper jaw plate and the upper jaw record base by means of a bonding agent;

after closing the adjustable articulator, coupling the lower jaw plate with the lower jaw record base by means of the bonding agent;

releasing said coupling shaft and after opening the adjustable articulator, removing said coupling device from said lower jaw plate and finishing the coupling of the two plates on the record bases individually for the preparation of a recording;

fixing the record bases of the upper jaw and the lower jaw in which the tracing device is assembled to teeth or to alveolar ridges in the oral cavity by means of an adhesive;

adjusting the positions of a guide support stud and a guide plate by shifting the lower jaw plate body;

after completing the adjustment of the occlusal vertical dimension, putting a plastic material on a guide plate and having the patient carry out the mandibular movement, forming a mandibular movement path and recording thereof;

furthermore, putting the plastic material on moving path forming tables, forming movement paths records by means of movement path forming auxiliary studs and recording thereof;

after inserting a tracing plate forming pin into a pin holding part, putting the plastic material on a tracing table, and forming a tracing plate having a slope by means of the tracing plate forming pin;

tracing a mandibular moving path on the surface of the tracing plate by means of a tracing pin and making small holes on the line of the mandibular moving path to fix the jaw relation;

fixing the jaw relation by fitting a jaw relation fitting pin into said small holes;

providing a contact having electric conductivity to the plate facing said jaw relation fixing pin, and then confirming a fixed condition of the jaw relation by means of an electric resistor; and pouring a material for checkbite between the upper jaw record base and the lower jaw record base, taking a checkbite core, adjusting the adjustable articulator using the obtained checkbite core, and as a result, replacing the records taken at the centric jaw relation and the border mandibular movement which is recorded in the oral cavity of the patient on the adjustable articulator.

* * * * *